United States Patent [19]

Zimmerschied et al.

[11] 4,271,312

[45] Jun. 2, 1981

[54] SUPPRESSION OF DIGLYCOL ETHER ESTER IN CHROMIUM (III) CATALYZED ETHYLENE OXIDE REACTION WITH AROMATIC CARBOXYLIC ACIDS

[75] Inventors: Wilford J. Zimmerschied; Delbert H. Meyer, both of Naperville, Ill.

[73] Assignee: Standard Oil Company (Indiana), Chicago, Ill.

[21] Appl. No.: 132,206

[22] Filed: Apr. 7, 1971

[51] Int. Cl.$^3$ .............................................. C07C 67/26
[52] U.S. Cl. .................................... 560/93; 560/80; 560/100; 560/112
[58] Field of Search ................ 260/475 P, 476, 486 B; 560/93, 80, 100, 112

[56] References Cited

U.S. PATENT DOCUMENTS

| | | | |
|---|---|---|---|
| 3,632,854 | 1/1972 | Randall | 260/475 P |
| 3,641,112 | 2/1972 | Ichikawa et al. | 260/475 P |
| 3,644,293 | 2/1972 | Fielder | 260/475 P |
| 3,873,602 | 3/1975 | Katzakian et al. | 260/475 P |
| 4,069,242 | 1/1978 | Gurgiolo | 560/93 |

FOREIGN PATENT DOCUMENTS 871767  6/1961  United Kingdom ................. 260/475 P

*Primary Examiner*—Jane S. Myers
*Attorney, Agent, or Firm*—Fred R. Ahlers; William T. McClain; William H. Magidson

[57] ABSTRACT

Chromium (III) catalysis of the reaction between ethylene oxides (ethylene oxide and 1,2-propylene oxide) and aromatic carboxylic acids at temperatures in the range from 50° to 180° C. are rapid but produce excessive amounts of diglycol ether ester (2-hydroxyethoxyethanol or 2-hydroxy-2-methylethoxy 2-methylethanol) which is present as the diglycol ether ester of the aromatic carboxylic acid and is a contaminent hard to remove from the desired 2-hydroxyethyl ester of the aromatic carboxylic acid. The use of an amine, in such ethylene oxide reaction with aromatic carboxylic acid suppresses the formation of diglycol ether and increases the conversion of aromatic carboxylic acid to the desired 2-hydroxyethyl ester thereof.

5 Claims, No Drawings

SUPPRESSION OF DIGLYCOL ETHER ESTER IN CHROMIUM (III) CATALYZED ETHYLENE OXIDE REACTION WITH AROMATIC CARBOXYLIC ACIDS

BACKGROUND OF THE INVENTION

Reaction between an ethylene oxide (e.g. ethylene oxide and 1,2-propylene oxide) and an aromatic carboxylic acid is known to proceed at a temperature upward from 50° C. and elevated pressure to maintain the ethylene oxide in the liquid phase to produce the corresponding 2-hydroxyethyl ester of the aromatic carboxylic acid without the attendant formation of by-product water as is the case when the corresponding glycol is used to esterify the acid. Reaction at 50° C. is slow but as would be expected, the reaction rate increases as reaction temperature is increased above 50° C. but reactions above 180° C. require apparatus to withstand the increased pressure necessary to maintain liquid phase conditions. Also as reaction temperature is increased there is an increased tendency of diglycol ether ester (e.g. 2-hydroxyethoxyethyl ester from ethylene oxide) formation by reaction between the ethylene oxide and the 2-hydroxyethyl ester. The diglycol ether ester (hereafter DGEE) of the aromatic carboxylic acid contaminates the desired 2-hydroxyethyl ester and is difficult to remove therefrom. The formation of DGEE contaminant is especially undesirable in 2-hydroxyethyl and 2-hydroxy-2-methylethyl esters of isophthalic acid, terephthalic acid and 1,1,3-trimethyl-3-(p-carboxyphenyl)-5-indane carboxylic acid which otherwise in the absence of DGEE can alone or in admixture be polycondensed to a fiber and film forming high molecular weight polyester. The presence of the DGEE causes formation of lower molecular weight polyester species which lower the thermal and oxidative stability of the final polyester product.

While the use of moderate temperatures of 100°–160° C. tend to suppress DGEE formation, rate of esterification of aromatic carboxylic acids with the ethylene oxide reactants is not commercially attractive in the absence of a catalyst. Amine catalysts such as ammonia, primary amines, secondary amines, tertiary amines, quaternary ammonium compounds (i.e. quaternary ammonium halides), N-heterocyclic amines; have been suggested as useful catalysts for example in French Pat. No. 1,428,204; British Pat. No. 623,669; U.S. Pat. No. 2,932,622 and U.S. Pat. No. 3,414,608. These patents also teach the use of inert reaction media such as water, acetone, methylethyl ketone, cyclohexanone, benzene, toluene, xylene, $C_6$ to $C_{10}$ alkane hydrocarbons, halogenated alkane hydrocarbons, ethers and preformed 2-hydroxyethyl esters including lower oligomers of the esters from dicarboxylic acids.

Chromium (III) catalysts (e.g. chromium octanoate) are broadly suggested for the reaction of aromatic carboxylic acids and oxirane compounds (i.e., ethylene and 1,2-propylene oxides) at temperatures of 25°–250° C. in Dutch Published Patent Application No. 67-01261, published July 27, 1967 and Belgian Pat. No. 715,201. Specific chromium (III) catalysts are organic compounds, for example Cr (III) 1-ethylpentane carboxylate, heptanecarboxylate, octanoate, oleate, cresylate, naphthenate, alkylbenzoate, alkoxybenzoate or chelate. Many of the above organic reaction media are also suggested as useful for this catalyzed reaction.

Our investigation of the catalytic effect of amine catalysts and chromium (III) catalysts with respect to aromatic acid esterification by ethylene and 1,2-propylene oxides indicated Cr (III) catalysts to produce a higher reaction rate (greater acid esterification in the same reaction time) at the same reaction temperatures but also produce DGEE at a higher rate. It has now been found that DGEE production enhanced by Cr (III) catalysts can be suppressed by the co-use of an amine without sacrifice of desired ester.

SUMMARY OF THE INVENTION

The inventive process comprises the preparation of 2-hydroxyethyl esters of aromatic carboxylic acid by their reaction with an ethylene oxide, such as ethylene oxide or 1,2-propylene oxide, in the presence of 0.5–2% chromium (III) catalyst based on the weight of the acid reactant and an amine present in an amount of 1.0 to 100% of the weight of the Cr (III) catalyst. The preferred Cr (III) catalysts are chromium (III) carboxylates of alkanoic monocarboxylic acids containing a total of 5 to 20 carbon atoms as illustrated by the pentane carboxylate, hexane carboxylate 1-ethyl heptyl carboxylate, heptanecarboxylate, octanecarboxylate, decane carboxylate, dodecanecarboxylate, hexadecane carboxylate naphthenates, oleate and stearates.

Such a process suppresses the Cr (III) catalysis of DGEE formation and, at the same time, increases the rate of esterification of aromatic acid to the 2-hydroxyethyl ester at temperatures over the range from 100° to 160° C. As will be demonstrated the co-use of Cr (III) catalyst and amine DGEE suppressant is not an additive effect with respect to the individual effects of Cr (III) catalyst and amine for either acid conversion to ester or DGEE formation.

The amine suppressant for Cr (III) DGEE formation can be any of the amines suggested as catalysts for aromatic acid esterification with an ethylene oxide. When the aromatic acid being esterified is a dicarboxylic acid and the resulting 2-hydroxyethyl ester is to be used in a polycondensation for the production of high molecular weight linear polyester, it is preferred to use a tertiary amine to suppress Cr (III) DGEE formation and not cause amide termination or interruption, especially the latter, of linear polyester formation. As such amines there can be mentioned trialkyl and trialicyclic amines, N-heterocyclic amines and N-alkyl-N-diarylamines and N-dialkyl N-arylamines. Illustrative thereof are triethylamine, tri-propylamine, tri-isopropylamine, tributylamines, triamylamines, tri-hexylamines, tri-heptylamines, trioctylamines, tri-decylamines, mixed trialkyl alkyl amines (e.g. N-di-methyl-N-ethyl amine), tricyclohexylamine, N-dimethyl cyclohexylamine, pyridine, N-dimethyl aniline, N-diethyl aniline, N-ethyl N-diphenylamine and N-ethyl N-cyclohexyl aniline.

The inventive process can be conducted in the inert reaction media before mentioned. When water is used as solvent a water-soluble Cr (III) catalyst is employed. However, the organic solvents are the preferred reaction media. Illustrative of these are the 2-hydroxyethyl ester products and, in the case of dicarboxylic acids, their lower oligomers (2–5 acid units), methyl ethyl ketone, methylisobutyl ketone, toluene and toluene and such ketone.

The amount of an ethylene oxide to be used in the inventive process is related to the aromatic carboxylic acid reactant. To further suppress DGEE formation from 0.9 to 1.1 equivalents of an ethylene oxide for each equivalent of aromatic acid is preferred. Thus, for an aromatic monocarboxylic acid (e.g., benzoic, toluic, 1-naphthalene carboxylic acid and the like 0.9–1.1 mole of an ethylene oxide is used per mole of such monocarboxylic acid. For aromatic dicarboxylic acids (e.g., isophthalic acid, terephthalic acid, 1,1,3-trimethyl-3-(p-carboxyphenyl)-5-indane carboxylic acid) and naphthalene dicarboxylic acids from 1.8 to 2.2 moles of an ethylene oxide is used with one mole of such dicarboxylic acid.

The following examples, comparative and illustrative, are given to demonstrate the advance and advantages of the present invention. In these examples terephthalic acid (TA) is esterified with ethylene oxide (ETO) in the presence of methyl isobutyl ketone as reaction medium. The Cr (III) catalyst, for example chromium octanoate (COT), and DGEE suppressant are used in the weight percent given based on TA for the mole ratio ETO/TA indicated. These examples and their results are shown in Table I below.

The additive effects expected from COT and TEA would be a total of 4.3% total DGEE instead of the 0.92% from the co-use of 1% each of COT and TEA. Thus the total DGEE suppression was not additive.

At the higher temperature of 160° C. the expected effect of co-use of COT and TEA on converted TA is additive with respect to the use COT or TEA alone but with respect to total DGEE the co-use of COT and TEA produces 2.84% DGEE which would be far less than the additive total DGEE expected from COT or TEA used alone.

The co-use of other tertiary amines with COT catalyst for the preparation of bis-(2-hydroxyethyl) terephthalate from ETO and TA may be expected to produce advantages comparable to the co-use of COT and TEA. Also for the co-use of a tertiary amine with COT catalyst for the reaction of TA or isophthalic acid with 1,2-propylene oxide there may be expected the advantages and advances illustrated above.

The tendency of ethylene oxide or 1,2-propylene

TABLE I

30 Minute Reactions of ETO and TA in Methyl Isobutyl Ketone in Presence of Cr (III) Catalyst

| Example | COT/ Weight % | Suppressant Weight % | ETO/TA Mole Ratio | Temperature °C. | TA Converted Mole % | DGEE Weight % |
|---|---|---|---|---|---|---|
| Comparative 1 | 1.0 | 0 | 2.1 | 120 | 50.8 | 6.06[2] |
| Comparative 2 | 1.0 | 0 | 2.1 | 160 | 82.0 | 5.80[2] |
| Comparative 3 | 0 | 1.0 TEA[1] | 2.0 | 120 | 24.3 | 0.10[2] |
| Comparative 4 | 0 | 1.0 TEA | 2.0 | 160 | 81.0 | 1.02[2] |
| Comparative 5 | 1.0 | 0 | 2.1 | 120 | 50.8 | 2.57[3] |
| Comparative 6 | 0 | 1.0 TEA | 2.0 | 160 | 81.0 | 0.43[3] |
| Comparative 7 | 1.0 | 1.0 NaCO3[4] | 2.0 | 120 | 38.3 | 2.43[3] |
| Comparative 8 | 1.0 | 1.0 NaOH | 2.0 | 160 | 59.5 | 2.22[3] |
| Illustrative 1 | 1.0 | 0.48 TEA | 2.1 | 120 | 63.9 | 1.51[2] |
| Illustrative 2 | 1.0 | 0.48 TEA | 2.0 | 160 | 96.6 | 2.84[2] |
| Illustrative 3 | 1.0 | 1.0 TEA | 2.1 | 120 | 71.7 | 0.92[2] |
| Illustrative 4 | 1.0 | 0.48 TEA | 2.1 | 120 | 63.9 | 0.64[3] |
| Illustrative 5 | 1.0 | 0.48 TEA | 2.0 | 160 | 96.6 | 1.20[3] |
| Illustrative 6 | 1.0 | 1.0 TEA | 2.1 | 120 | 71.7 | 0.39[3] |

[1]TEA is triethylamine
[2]Total DGEE as 2-hydroxyethoxyethyl 2-hydroxyethyl terephthalate mixed ester, bis-(2-hydroxyethoxyethyl) terephthalate and etherester equivalent based on ester product.
[3]DGEE as diethylene glycol only based on ester product
[4]20 Minute reaction.

From a comparison of TA conversion and DGEE from Examples Comparative 7 and 8 against Examples Illustrative 4, 5 and 6, it is indeed surprising that from the use of TEA as suppressant the TA conversions are higher and DGEE formations are lower than when Na₂CO₃ and NaOH are used as DGEE suppressants.

From comparisons of TA conversions from Examples Illustrative 1–6 against Comparative 1–6, it is observed that in each case the TA conversions are substantially higher and from comparisons of DGEE formation, the use of TEA and COT always produced lower DGEE than use of COT alone.

Next, there can be evaluated the individual effects of 1% COT, 1% TEA as catalyst and co-use of 1% of each of COT and TEA at 120° C. from Examples Comparative 1, Comparative 3 and Illustrative 3. With respect to TA conversion and based on 100 moles TA, COT provides 50.8 moles converted TA, TEA would be expected to provide of the remaining 49.2 moles another 11.96 moles (49.2×0.243) converted TA or a total of 62.76 moles converted TA. But the use of 1% each of COT and TEA provided 71.7 moles converted TA which is an improvement of 12.5% over said expected additive effect from COT and TEA used alone. Then with respect to total DGEE, 1% COT produced 6.06% DGEE, and 1% TEA alone produced 0.1% DGEE.

oxide to react respectively with first formed 2-hydroxyethyl or 2-hydroxy-2-methylether ester and from DGEE is not substantially changed with the charge of acid reactant from TA to isophthalic acid, or to benzoic acid or to 1,4-naphthalene dicarboxylic acid, or to 1,5-naphthalene dicarboxylic acid or to 1,1,3-trimethyl-3-(p-carboxyphenyl)-5-indane carboxylic acid or to any other aromatic carboxylic acid.

The invention claimed is:

1. A process for the preparation of 2-hydroxyethyl esters of aromatic carboxylic acids which comprises reacting at a temperature in the range of 100° to 160° C. substantially equivalent proportions of an aromatic carboxylic acid and ethylene oxide or 1,2-propylene oxide in the presence of chromium (III) octanoate and triethylamine, wherein chromium octanoate is present in an amount in the range from 0.5 to 2% based on the weight of said aromatic acid and triethylamine is present in the range from 50 to 100% of the weight of the chromium octanoate.

2. The process of claim 1 wherein the aromatic carboxylic acid is isophthalic acid or terephthalic acid or mixtures thereof or 1,1,3-trimethyl-3-(p-carboxyphenyl)-5-indane carboxylic acid.

3. The process of claim 1 wherein the reaction is conducted in the presence of a reaction medium comprising water, preformed 2-hydroxyethyl ester, a benzene hydrocarbon, an aliphatic ketone or an alkane hydrocarbon containing 6 to 10 carbon atoms.

4. The process of claim 2 wherein the reactants are terephthalic acid and ethylene oxide used in a 1:2 mole ratio, the reaction medium is methylisobutyl ketone and the reaction temperature is in the range from 120° to 160° C.

5. The process of claim 2 wherein the reactants are isophthalic acid and ethylene oxide used in a 1:2 mole ratio, the reaction medium is methylisobutyl ketone and the reaction temperature is in the range from 120° to 160° C.

* * * * *

UNITED STATES PATENT OFFICE
CERTIFICATE OF CORRECTION

Patent No. 4,271,312  Dated June 2, 1981

Inventor(s) Wilford J. Zimmerschied and Delbert H. Meyer

It is certified that error appears in the above-identified patent and that said Letters Patent are hereby corrected as shown below:

| Patent Column | Line | |
|---|---|---|
| abstract | 18 | "contaminent" should be -- contaminant -- |
| 2 | 29-30 | "2-hydrox-yethyl" should be -- 2-hydroxy-ethyl -- |
| 2 | 50 | "tri-hexylamines,," should be -- tri-hexylamines, -- |
| 2 | 52-53 | "trialkyl alkyl amines" should be -- trialkyl amines -- |
| 3 | 3 | "the like 0.9-1.1 mole" should be -- the like) 0.9-1.1 mole -- |
| 4 | 7 | "the use COT" should be -- the use of COT -- |

Signed and Sealed this

Twenty-seventh Day of October 1981

[SEAL]

Attest:

GERALD J. MOSSINGHOFF

Attesting Officer  Commissioner of Patents and Trademarks